(12) United States Patent
Xie et al.

(10) Patent No.: US 10,821,036 B2
(45) Date of Patent: Nov. 3, 2020

(54) PERFORATED NON-WOVEN FABRIC AND PRODUCTION METHOD THEREOF

(71) Applicant: Xiamen Yanjan New Material Co., Ltd., Xiamen (CN)

(72) Inventors: Jihua Xie, Xiamen (CN); Jixiang Cai, Xiamen (CN)

(73) Assignee: XIAMEN YANJAN NEW MATERIAL CO., LTD., Xiamen, Fujian (CN)

( * ) Notice: Subject to any disclaimer, the term of this patent is extended or adjusted under 35 U.S.C. 154(b) by 121 days.

(21) Appl. No.: 15/744,078

(22) PCT Filed: Aug. 10, 2016

(86) PCT No.: PCT/CN2016/094311
§ 371 (c)(1),
(2) Date: Jan. 12, 2018

(87) PCT Pub. No.: WO2017/156969
PCT Pub. Date: Sep. 21, 2017

(65) Prior Publication Data
US 2018/0200123 A1 Jul. 19, 2018

(30) Foreign Application Priority Data
Mar. 16, 2016 (CN) .......................... 2016 1 0148875

(51) Int. Cl.
*B32B 3/24* (2006.01)
*A61F 13/512* (2006.01)
(Continued)

(52) U.S. Cl.
CPC .... *A61F 13/5123* (2013.01); *A61F 13/15707* (2013.01); *A61F 13/5121* (2013.01);
(Continued)

(58) Field of Classification Search
CPC ............. B32B 3/266; Y10T 428/24281; A61F 13/5121
(Continued)

(56) References Cited

U.S. PATENT DOCUMENTS

| 5,635,276 A * | 6/1997 | Biagioli | B29D 99/0089 428/132 |
| 8,784,972 B2 * | 7/2014 | Sato | B32B 3/266 428/166 |

FOREIGN PATENT DOCUMENTS

JP 2004129924 A * 4/2004

\* cited by examiner

*Primary Examiner* — William P Watkins, III
(74) *Attorney, Agent, or Firm* — Leong C. Lei

(57) ABSTRACT

Provided are a perforated non-woven fabric and a production method thereof. The perforated non-woven fabric is formed by overlapping three-dimensional funnel-shaped openings of two perforated non-woven fabric layers. The first perforated non-woven fabric layer has a protruding portion and a recessed portion. The protruding portion has an internal space. An upper side of the second perforated non-woven fabric layer is adhered to a lower side of the recessed portion of the first perforated non-woven fabric layer. The overlapped three-dimensional funnel-shaped openings pass through the first perforated non-woven fabric layer and the second perforated non-woven fabric layer. An air flow passage is formed between continuous internal spaces of the protruding portions of the first perforated non-woven fabric layer and the second perforated non-woven fabric layer, thereby facilitating penetration of liquid and soft feces, reducing residues, enabling internal and external air flow circulation, and reducing discomfort from wetness.

13 Claims, 9 Drawing Sheets

(51) Int. Cl.
    *A61F 13/15*         (2006.01)
    *B32B 3/26*          (2006.01)
    *B32B 3/30*          (2006.01)
    *B32B 5/02*          (2006.01)
    *B32B 5/26*          (2006.01)
    *B32B 7/12*          (2006.01)
    *B32B 37/00*        (2006.01)
    *B32B 37/10*        (2006.01)
    *B32B 38/04*        (2006.01)
    *B32B 38/06*        (2006.01)
    *A61F 13/513*      (2006.01)
    *B32B 37/06*        (2006.01)
    *B32B 37/20*        (2006.01)

(52) U.S. Cl.
    CPC ................ *B32B 3/266* (2013.01); *B32B 3/30* (2013.01); *B32B 5/022* (2013.01); *B32B 5/26* (2013.01); *B32B 7/12* (2013.01); *B32B 37/0053* (2013.01); *B32B 37/10* (2013.01); *B32B 38/04* (2013.01); *B32B 38/06* (2013.01); *A61F 2013/15878* (2013.01); *A61F 2013/51338* (2013.01); *A61F 2013/51355* (2013.01); *B32B 37/06* (2013.01); *B32B 37/20* (2013.01); *B32B 2038/047* (2013.01); *B32B 2250/20* (2013.01); *B32B 2307/724* (2013.01); *B32B 2307/73* (2013.01); *B32B 2555/02* (2013.01)

(58) Field of Classification Search
    USPC .................................................. 428/154, 132
    See application file for complete search history.

PERFORATED NON-WOVEN FABRIC AND PRODUCTION METHOD THEREOF

BACKGROUND OF THE INVENTION

1. Field of the Invention

The present invention relates to a non-woven fabric, and more particularly to a perforated non-woven fabric having three-dimensional funnel-shaped openings and air flow passages and a production method thereof.

2. Description of the Prior Art

Non-woven fabrics are soft, skin-friendly and breathable, and are widely used in sanitary products, such as sanitary napkins, diapers and the like, cleaning supplies, masks, medical supplies, and so on. However, the use of sanitary napkins or diapers, the body fluids may contain clots or baby soft will be attached to the surface of the sanitary napkin or diaper, thus greatly reducing the comfort and breathability of sanitary products.

Chinese Patent Publication No. CN2010101842233 describes a composite sheet in which a large number of convex portions made of an upper fiber sheet are provided on a substantially flat lower fiber sheet by three-dimensionally shaping the upper fiber sheet. Concave portions are provided between the convex portions. The concave portions and the convex portions are arranged in an interlaced manner on the composite sheet. The interlaced arrangement of the concave portions and the convex portions can effectively prevent liquid leakage. In particular, when the excrement is soft excrement having a high viscosity. The soft stool is caught in the closed concave portions surrounded by the convex portions, so that the excrement is less likely to flow laterally. However, since the two-layered non-woven fabric is bonded through the bonding area of the concave portions, the bonding point and the bonding area of the concave portions thicken the non-woven fabric. This hinders the excrement, especially high-viscosity excrement, from infiltrating into the absorbent, and the soft stool stays on the bonding area of the concave portions. The strength of the convex portions is insufficient to support the pressure of the baby's body weight so that the soft stool will stick to the baby's skin during use of the diaper, which is likely to cause diaper rash.

By using the production method of Chinese Patent Publication No. CN2010101842233, since the non-woven fabric itself is easily stretched and deformed under tension, the convex portions of the non-woven fabric may move during the production and are bonded to the concave portions to break the convex portions. Therefore, it is necessary to add a suction system on two rollers so that the fiber sheet can be attached to the periphery of the roller to fix the convex portions. Since the breathability of the non-woven fabric is very good, it requires a relatively large pumping capacity, resulting in high production cost and high difficulty.

SUMMARY OF THE INVENTION

The primary object of the present invention is to overcome the drawbacks of the prior art and provide a non-woven fabric capable of improving the penetration ability of the non-woven fabric while maintaining its three-dimensional structure and a production method thereof.

According to one aspect of the present invention, a perforated non-woven fabric is provided. The perforated non-woven fabric is formed by overlapping three-dimensional funnel-shaped openings of first and second perforated non-woven fabric layers. The first perforated non-woven fabric layer has a protruding portion and a recessed portion. The protruding portion has an internal space. An upper side of the second perforated non-woven fabric layer is bonded to a lower side of the recessed portion of the first perforated non-woven layer. The overlapped three-dimensional funnel-shaped openings pass through the first perforated non-woven fabric layer and the second perforated non-woven fabric layer.

Preferably, an upper surface of the protruding portion forms a continuous plane so that a continuous air flow passage is formed between the continuous internal space of the protruding portion of the first perforated non-woven fabric layer and the second perforated non-woven fabric layer.

Preferably, the protruding portion and the recessed portion are arranged by turns. The protruding portion has an independent discontinuous internal space. An independent discontinuous air flow passage is formed between the independent discontinuous internal space of the protruding portion of the first perforated non-woven fabric layer and the second perforated non-woven fabric layer.

Preferably, the protruding portion of the first perforated non-woven fabric layer has an opening structure.

Preferably, the three-dimensional funnel-shaped openings each extend from a top thereof toward a bottom thereof.

Alternatively, the three-dimensional funnel-shaped openings each extend from a bottom thereof toward a top thereof.

Preferably, a diameter of a top of the three-dimensional funnel-shaped openings is 0.2-5 mm.

Preferably, a diameter of a top of the three-dimensional funnel-shaped openings is at least 20% greater than a diameter of a bottom of the three-dimensional funnel-shaped openings.

Preferably, the area of a top of the three-dimensional funnel-shaped openings accounts for less than 70% of the total area of the perforated non-woven fabric.

Preferably, the three-dimensional funnel-shaped openings have a height of 0.1-5 mm.

Preferably, the first perforated non-woven fabric layer is a water-repellent non-woven fabric, and the second perforated non-woven fabric layer is a hydrophilic non-woven fabric.

Preferably, the first perforated non-woven fabric layer or/and the second perforated non-woven fabric layer are one of a hot-blast non-woven fabric, a spunbond non-woven fabric and a spunlace non-woven fabric.

Preferably, a bonding of the recessed portion is a thermal bonding region or a glue bonding region.

According to another aspect of the present invention, a production method for producing the aforesaid perforated non-woven fabric adopts hot bonding. After the first perforated non-woven fabric layer is embossed and punched on a pair of concave and convex rollers, the first perforated non-woven fabric layer is closely attached to the convex roller by means of the temperature of the convex roller and a piercing process of a needle tip on the convex roller and then bonded to the second perforated non-woven fabric layer by means of punching and hot rolling of a third concave roller.

According to a further aspect of the present invention, a production method for producing the aforesaid perforated non-woven fabric adopts hot bonding. After the first perforated non-woven fabric layer is embossed and punched on a pair of concave and convex rollers, the non-woven fabric is first punched by means of the temperature of the convex roller and a salient point on the convex roller. The first perforated non-woven fabric layer is closely attached to the convex roller by means of the temperature of the convex roller and a piercing process of a needle tip on the convex roller. The convex roller meshes with a third concave roller. The salient point on the convex roller is pressed in a recess of the third concave roller. The first perforated non-woven fabric layer and the second perforated non-woven fabric layer are embossed and hot rolled by the third concave roller to be bonded. The first perforated non-woven fabric layer and the second perforated non-woven fabric layer are pressed into a recessed hole of the third concave roller through the salient point. The first perforated non-woven fabric layer and the second perforated non-woven fabric layer are simultaneously transferred to the third concave roller and then are punched by a fourth needle roller.

According to a yet further aspect of the present invention, a production method for producing the aforesaid perforated non-woven fabric adopts glue bonding. After the first perforated non-woven fabric layer is embossed and punched on a pair of concave and convex rollers, the first perforated non-woven fabric layer is closely attached to the convex roller by means of the temperature of the convex roller and a piercing process of a needle tip on the convex roller. The first perforated non-woven fabric layer and the second perforated non-woven fabric layer are punched by a third concave roller. The second perforated non-woven fabric layer is glued before the second perforated non-woven fabric layer passes through the third concave roller to be punched.

With the above technical scheme, the perforated non-woven fabric of the present invention is formed by overlapping three-dimensional funnel-shaped openings of two perforated non-woven fabric layers. The air flow passage is formed between the continuous internal space of the protruding portion of the first perforated non-woven fabric layer and the second perforated non-woven fabric layer. The non-woven fabric not only maintains the convex three-dimensional structure but also provides a permeable air flow passage, thereby speeding up the infiltration of the liquid, excrement, and soft stool and reducing the residual. The bonding of the two perforated non-woven fabric layers prevents the protruding portion from being compressed to effectively form the air flow passage so as to prevent the air flow passage from being clogged and crushed, providing the internal and external circulation of the air flow and reducing the feeling of wetness. The three-dimensional funnel-shaped opening structure enables the non-woven fabric to have a certain distance from the lower absorbent. The funnel-shaped opening structure effectively prevents the liquid from flowing back. The first perforated non-woven fabric layer is closely attached to the convex roller through the piercing process of the needle tip during the process, so that the first non-woven fabric layer and the second non-woven fabric layer won't be dislocated during the bonding process, thereby simplifying the process and saving manufacturing costs.

DETAILED DESCRIPTION OF THE PREFERRED EMBODIMENTS

Figure 1:
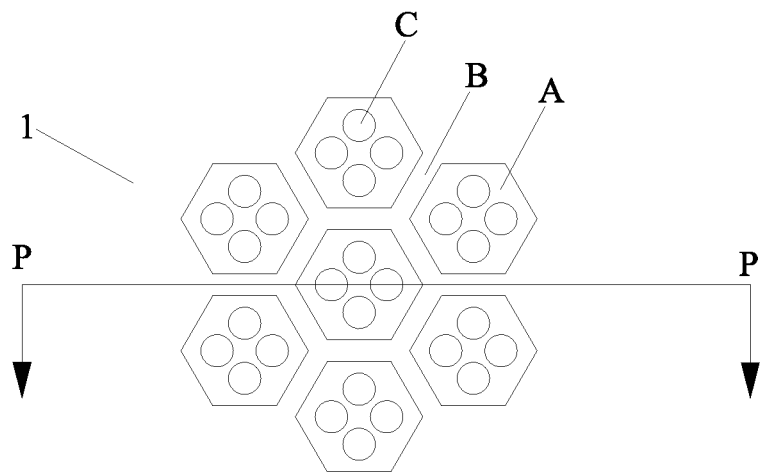
FIG. 1 is a top view of a perforated non-woven fabric in accordance with a first embodiment of the present invention.

Embodiments of the present invention will now be described, by way of example only, with reference to the accompanying drawings.

As shown in FIG. 1 to FIG. 9, the present invention discloses a perforated non-woven fabric. The perforated non-woven fabric is formed by overlapping three-dimensional funnel-shaped openings of two perforated non-woven fabric layers 11, 12. The first perforated non-woven fabric layer 11 has a protruding portion B and a recessed portion A. The protruding portion B has an internal space E. An upper side of the second perforated non-woven fabric layer 12 is bonded to a lower side of the recessed portion A of the first perforated non-woven layer 11. The overlapped three-dimensional funnel-shaped openings extend from the recessed portion A of the first perforated non-woven fabric layer 11 toward a lower side of the second perforated non-woven fabric layer 12 or extend from the lower side of the second perforated non-woven fabric layer 12 toward the recessed portion A of the first perforated non-woven fabric layer 11 to pass through the first perforated non-woven fabric layer 11 and the second perforated non-woven fabric layer 12. The upper surface of the protruding portion B is a continuous plane or discontinuous plane so as to form a continuous internal space or an isolated internal space between the first perforated non-woven fabric layer 11 and the second perforated non-woven fabric layer 12 of the non-woven fabric. The diameter of the top of the three-dimensional funnel-shaped opening is 0.2-5 mm. The diameter of the top of the three-dimensional funnel-shaped opening is at least 20% greater than the diameter of the bottom of the three-dimensional funnel-shaped opening. The area of the top of the three-dimensional funnel-shaped opening accounts for less than 70% of the total area of the perforated non-woven fabric. The three-dimensional funnel-shaped opening has a height of 0.1-5 mm.

Porosity test method is as follows:

Measuring instruments: Shanghai rectangular XTL-200 electron microscope (connected to the computer), CF-2000MIS image analysis system.

1. Turn on the CF-2000MIS image analysis system, adjust the magnification of 1.0 and calibrate. Place the sample under the lens, turn on the light source. When the light source is adjusted to a threshold of 95, two peaks appear in the histogram.

2. Click the "capture image" icon, adjust the focus for the image to achieve the clearest result, and click the "freeze image" icon for image acquisition. Click the "measure rectangle parameters" icon to draw a rectangle with five holes therein. The size of the rectangle is 7500×7500 µm. Click the "adjust the position of the measuring rectangle" icon to fine-tune the rectangle, and then click the "merge the measuring mark with the image" icon to merge the rectangle with the image.

3. Click the "select rectangle area" icon, select the same rectangular area, and then click the "analysis target selection and coloring" icon. The "analysis target confirmation" dialog box appears. Adjust the threshold to 95 and click confirmation. Click the "processing" button, select "smooth inside and outside of analysis target", and click the "smooth inside and outside of analysis target" to deal with the picture. Then click "lasso target selection tool" to deal with the coloring of other than 5 holes.

4. Click the "target analysis" icon to appear the "analysis result-visual processing" dialog box, and click the "analysis" button to appear the "single parameter analysis" dialog box. In the calculation options, select "algebra and/analysis area" as the current calculation option. Click the "calculate" button, the analysis result A will be displayed in the dialog box. A×100% is the porosity, and the result is accurate to 0.1%.

The height h of the three-dimensional funnel-shaped openings C, D is 0.5 mm, so the non-woven fabric has a better three-dimensional effect. The perforated non-woven fabric 1 is separated from the lower core. The upper diameter of the openings C, D is 1.3 mm, and the lower diameter of the openings C, D is 0.8 mm. The d/r is 1.6. The funnel-shaped structure allows the liquid to infiltrate down quickly and can effectively prevent the liquid from flowing back.

The test method for the height and the diameter of the three-dimensional funnel-shaped opening is as follows:

Measuring instruments: Shanghai rectangular XTL-200 electron microscope (connected to the computer), CF-2000MIS image analysis system;

Sample Preparation: Use a pair of scissors to cut a sample along the direction of MD. Make sure that the three-dimensional funnel-shaped opening at the edge is intact, and attach the sample to the mold;

Test steps:

1) Size Calibration: open the 1.5× calibration image and click the "size calibration" icon to pull the standard ruler to the correct position and click "confirm".

2) Image Acquisition: open the CF-2000MIS image analysis system, select the magnification 1.5 times, and place the sample under the microscope. The sample is placed on the mold and faces up. Turn on the light source, and click the "acquire Image" icon to adjust the focus until the image is clear to ensure that the operator can see 3-4 holes in the image, and then click the "freeze image" icon for image acquisition.

3) Measurement: click the "measure linear geometry parameter" icon to draw a horizontal line on the bottom surface of the three-dimensional funnel-shaped opening of the sample and draw a vertical line from the top surface of the three-dimensional funnel-shaped opening to the horizontal line. The value is the height of the three-dimensional funnel-shaped opening. The value is accurate to 0.01 mm.

First Embodiment

Figure 1A:
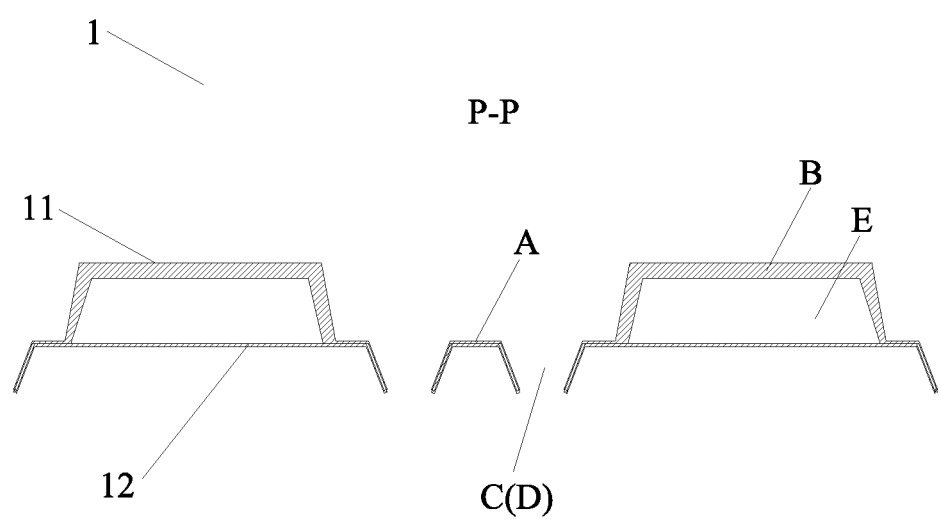
FIG. 1A is a sectional view taken along line P-P of FIG. 1.

As shown in FIG. 1 and FIG. 1A, a perforated non-woven fabric 1 is formed by bonding two perforated non-woven fabric layers 11, 12. The first perforated non-woven fabric layer 11 has a protruding portion B and a recessed portion A to be in contact with the user's skin. The protruding portion B may be a continuous plane. The recessed portion A is disposed in the protruding portion B in the form of "sea". A three-dimensional funnel-shaped opening C of the first perforated non-woven fabric layer 11 is disposed in the recessed portion A. An upper side of the second perforated non-woven fabric layer 12 is bonded to a lower side of the recessed portion A of the first perforated non-woven layer 12. A three-dimensional funnel-shaped opening D of the second perforated non-woven fabric layer overlaps the three-dimensional funnel-shaped opening C of the first perforated non-woven fabric layer to pass through the entire non-woven fabric 1. The protruding portion B of the first perforated non-woven fabric layer 11 has a continuous internal space E. The continuous internal space E forms a continuous air flow passage between the first perforated non-woven fabric layer 11 and the second perforated non-woven fabric layer 12 to pass through the entire non-woven fabric 1. The bonding area of the two non-woven fabric layers fixedly supports the air flow passage so that the air flow passage has strong compressive strength. After the pressure is released, the air flow passage is rapidly restored, so that the air flow inside the perforated non-woven fabric 1 convects with the outside air, allowing the air to circulate. In this way, the protruding area in contact with the skin surface can bring a soft touch to the user, maintain the 3D visual effect of the three-dimensional non-woven fabric, reduce the feeling of wetness and stuffiness, and improve the comfort effect.

The diameter of the top of the overlapped three-dimensional funnel-shaped openings C, D is 1.0 mm. The diameter R of the top of the three-dimensional funnel-shaped opening is at least 30% greater than the diameter r of the bottom of the three-dimensional funnel-shaped opening. The area of the top of the three-dimensional funnel-shaped opening accounts for 30% of the total area of the perforated non-woven fabric. The three-dimensional funnel-shaped opening has a height of 1 mm. The overlapped three-dimensional funnel-shaped openings C, D allow feces to quickly penetrate into the absorbent from the overlapped three-dimensional funnel-shaped openings C, D. The shape of the openings may be various geometric shapes, such as a circle, a square, a rectangle, or a combination thereof. When the bodily fluid flows along the protruding portion B to the openings, the three-dimensional funnel-shaped openings C, D have a guiding effect and allow the bodily liquid to rapidly penetrate into the absorbent from the openings, thereby improving the dryness of the absorbent article and also promoting the fast absorption of the bodily fluid.

Second Embodiment

Figure 2:
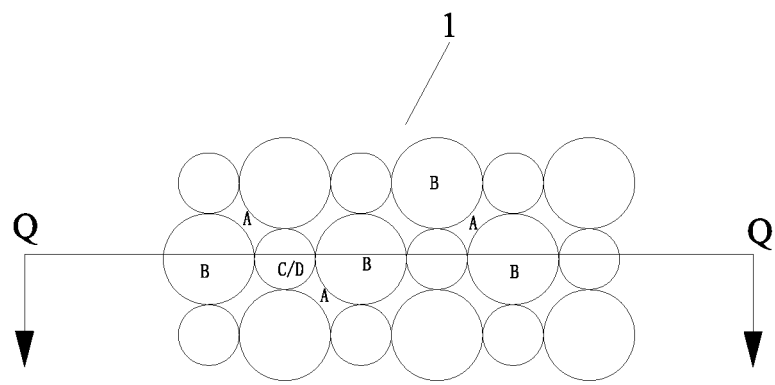
FIG. 2 is a top view of a perforated non-woven fabric in accordance with a second embodiment of the present invention.
Figure 2A:
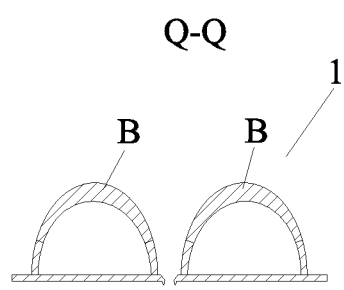
FIG. 2A is a sectional view taken along line Q-Q of FIG. 2.

As shown in FIG. 2 and FIG. 2A, a perforated non-woven fabric 1 is formed by bonding two perforated non-woven fabric layers 11, 12. The first perforated non-woven fabric layer 11 has a protruding portion B and a recessed portion A to be in contact with the user's skin. Seen from the top view, the protruding portion B is like an isolated "island", and the recessed portion A surrounds the protruding portion B in the form of "sea". A three-dimensional funnel-shaped opening C of the first perforated non-woven fabric layer 11 is disposed in the recessed portion A. An upper side of the second perforated non-woven fabric layer 12 is bonded to a lower side of the recessed portion A of the first perforated non-woven layer 12. A three-dimensional funnel-shaped opening D of the second perforated non-woven fabric layer overlaps the three-dimensional funnel-shaped opening C of the first perforated non-woven fabric layer to pass through the entire non-woven fabric 1 and surround the protruding portion B. The protruding portion B of the first perforated non-woven fabric layer 11 has an independent internal space E. The independent internal space E forms an independent air flow passage between the first perforated non-woven fabric layer 11 and the second perforated non-woven fabric layer 12. The bonding area of the two non-woven fabric layers fixedly supports the air flow passage so that the air flow passage has strong compressive strength. In this way, the protruding area can maintain the 3D visual effect of the three-dimensional non-woven fabric, reduce the feeling of wetness and stuffiness, and improve the comfort effect. The diameter of the top of the overlapped three-dimensional funnel-shaped openings C, D is 1.5 mm. The diameter R of the top of the three-dimensional funnel-shaped opening is at least 25% greater than the diameter r of the bottom of the three-dimensional funnel-shaped opening. The area of the top of the three-dimensional funnel-shaped opening accounts for 25% of the total area of the perforated non-woven fabric. The three-dimensional funnel-shaped opening has a height of 0.5 mm. The overlapped three-dimensional funnel-shaped openings C, D allow feces to quickly penetrate into the absorbent from the overlapped three-dimensional funnel-shaped openings C, D. The shape of the openings may be various geometric shapes, such as a circle, a square, a rectangle, and a combination thereof. When the bodily fluid flows along the protruding portion B to the openings, the three-dimensional funnel-shaped openings C, D have a guiding effect and allow the bodily liquid to rapidly penetrate into the absorbent from the openings, thereby improving the dryness of the absorbent article and also promoting the fast absorption of the bodily fluid.

Third Embodiment

Figure 3:
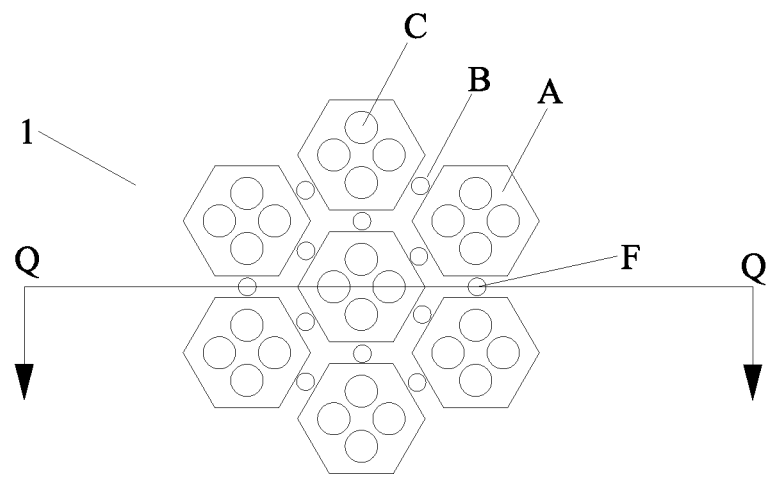
FIG. 3 is a top view of a perforated non-woven fabric in accordance with a third embodiment of the present invention.
Figure 3A:
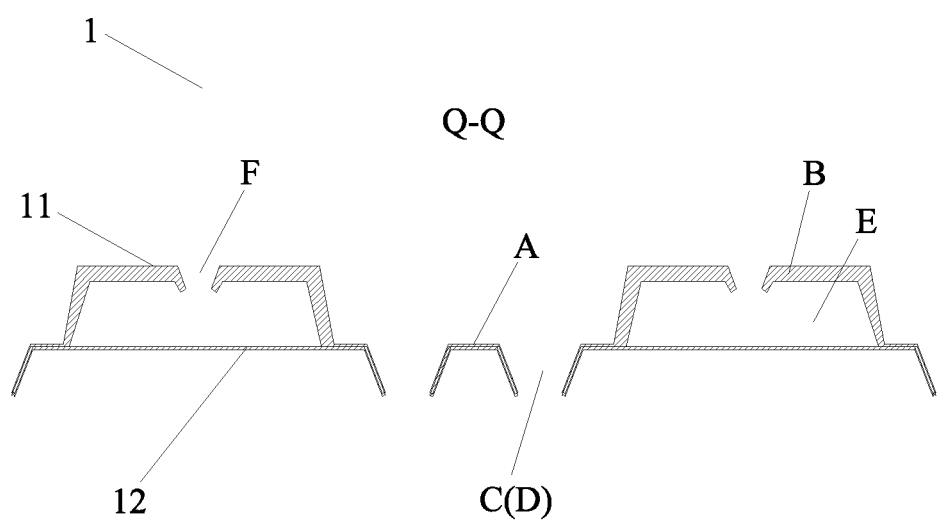
FIG. 3A is a sectional view taken along line S-S of FIG. 3.

As shown in FIG. 3 and FIG. 3A, a perforated non-woven fabric 1 is formed by bonding two perforated non-woven fabric layers 11, 12. The first perforated non-woven fabric layer 11 has a protruding portion B and a recessed portion A to be in contact with the user's skin. Seen from the top view, the protruding portion B is a continuous plane. The recessed portion A is disposed in the protruding portion B in the form of "sea". A three-dimensional funnel-shaped opening F is disposed in the protruding portion B. An upper side of the second perforated non-woven fabric layer 12 is bonded to a lower side of the recessed portion A of the first perforated non-woven layer 12. A three-dimensional funnel-shaped opening D of the second perforated non-woven fabric layer overlaps the three-dimensional funnel-shaped opening C of the first perforated non-woven fabric layer to pass through the entire non-woven fabric 1. The protruding portion B of the first perforated non-woven fabric layer 11 has a continuous internal space E. The continuous internal space E forms a continuous air flow passage between the first perforated non-woven fabric layer 11 and the second perforated non-woven fabric layer 12 to pass through the entire non-woven fabric 1. The bonding area of the two non-woven fabric layers fixedly supports the air flow passage so that the air flow passage has strong compressive strength. After the pressure is released, the air flow passage is rapidly restored, so that the air flow inside the perforated non-woven fabric 1 convects with the outside air, allowing the air to circulate. In this way, the protruding area in contact with the skin surface can bring a soft touch to the user, maintain the 3D visual effect of the three-dimensional non-woven fabric, reduce the feeling of wetness and stuffiness, and improve the comfort effect. The diameter of the top of the overlapped three-dimensional funnel-shaped openings C, D is 2.0 mm. The diameter R of the top of the three-dimensional funnel-shaped opening is at least 40% greater than the diameter r of the bottom of the three-dimensional funnel-shaped opening. The area of the top of the three-dimensional funnel-shaped opening accounts for 30% of the total area of the perforated non-woven fabric. The three-dimensional funnel-shaped opening has a height of 0.8 mm. The overlapped three-dimensional funnel-shaped openings C, D allow feces to quickly penetrate into the absorbent from the overlapped three-dimensional funnel-shaped openings C, D. The first perforated non-woven fabric layer has the three-dimensional funnel-shaped opening F, which not only makes the protruding portion more breathable and but also forms the air flow passage more easily. When the bodily fluid flows along the protruding portion B to the openings, the three-dimensional funnel-shaped openings C, D and the three-dimensional funnel-shaped opening F have a guiding effect and allow the bodily liquid to rapidly penetrate into the absorbent from the openings, thereby improving the dryness of the absorbent article and also promoting the fast absorption of the bodily fluid.

Fourth Embodiment

Figure 4:
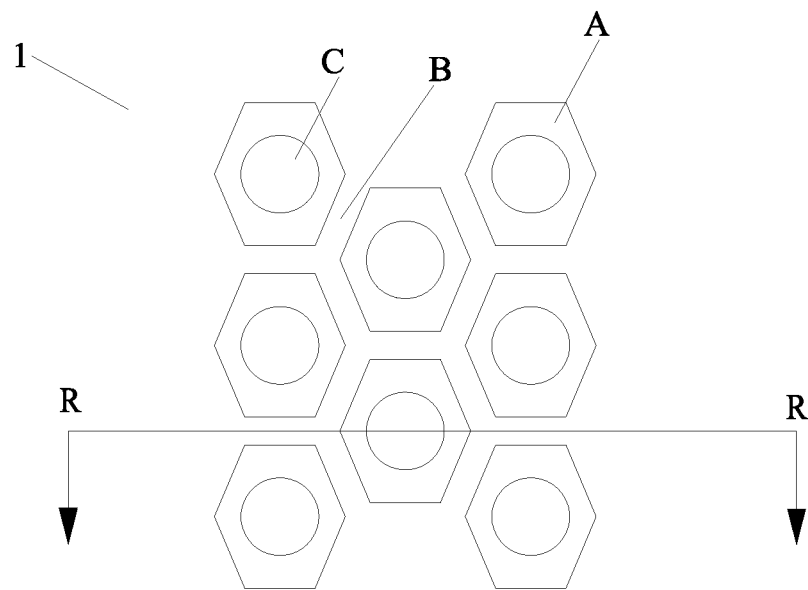
FIG. 4 is a top view of a perforated non-woven fabric in accordance with a fourth embodiment of the present invention.
Figure 4A:
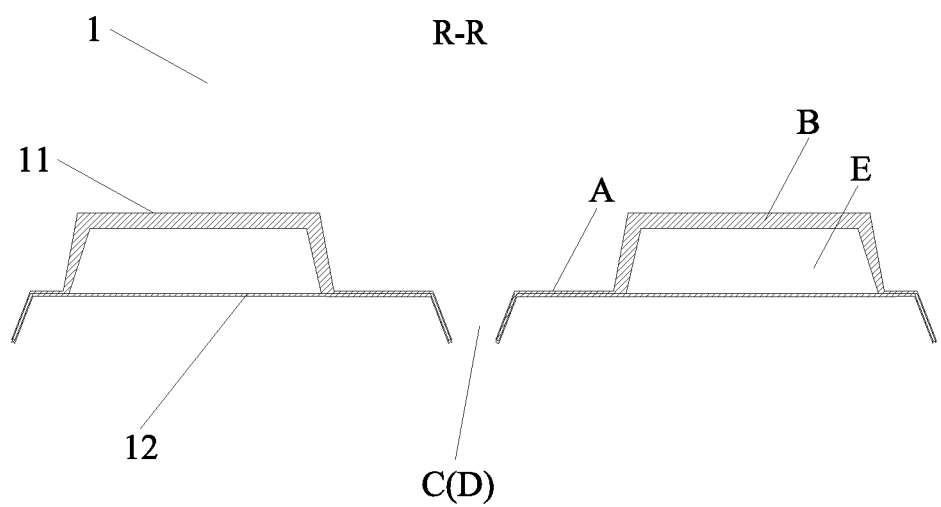
FIG. 4A is a sectional view taken along line R-R of FIG. 4.

As shown in FIG. 4 and FIG. 4A, a perforated non-woven fabric 1 is formed by bonding two perforated non-woven fabric layers 11, 12. The first perforated non-woven fabric layer 11 has a protruding portion B and a recessed portion A to be in contact with the user's skin. Seen from the top view, the protruding portion B is a continuous plane. The recessed portion A is disposed in the protruding portion B in the form of "sea". A three-dimensional funnel-shaped opening C of the first perforated non-woven fabric layer 11 is disposed in the recessed portion A. An upper side of the second perforated non-woven fabric layer 12 is bonded to a lower side of the recessed portion A of the first perforated non-woven fabric layer 12. A three-dimensional funnel-shaped opening D of the second perforated non-woven fabric layer overlaps the three-dimensional funnel-shaped opening C of the first perforated non-woven fabric layer to pass through the entire non-woven fabric 1. The protruding portion B of the first perforated non-woven fabric layer 11 has a continuous internal space E. The continuous internal space E forms a continuous air flow passage between the first perforated non-woven fabric layer 11 and the second perforated non-woven fabric layer 12 to pass through the entire non-woven fabric 1. The bonding area of the two non-woven fabric layers fixedly supports the air flow passage so that the air flow passage has strong compressive strength. After the pressure is released, the air flow passage is rapidly restored, so that the air flow inside the perforated non-woven fabric 1 convects with the outside air, allowing the air to circulate. In this way, the protruding area in contact with the skin surface can bring a soft touch to the user, maintain the 3D visual effect of the three-dimensional non-woven fabric, reduce the feeling of wetness and stuffiness, and improve the comfort effect. The diameter of the top of the overlapped three-dimensional funnel-shaped openings C, D is 2.5 mm. The diameter R of the top of the three-dimensional funnel-shaped opening is at least 40% greater than the diameter r of the bottom of the three-dimensional funnel-shaped opening. The area of the top of the three-dimensional funnel-shaped opening accounts for 28% of the total area of the perforated non-woven fabric. The three-dimensional funnel-shaped opening has a height of 1.2 mm. The overlapped three-dimensional funnel-shaped openings C, D allow feces to quickly penetrate into the absorbent from the overlapped three-dimensional funnel-shaped openings C, D. The shape of the openings may be various geometric shapes, such as a circle, a square, a rectangle, or a combination thereof. When the bodily fluid flows along the protruding portion B to the openings, the three-dimensional funnel-shaped openings C, D have a guiding effect and allow the bodily liquid to rapidly penetrate into the absorbent from the openings, thereby improving the dryness of the absorbent article and also promoting the fast absorption of the bodily fluid.

Fifth Embodiment

Figure 5:
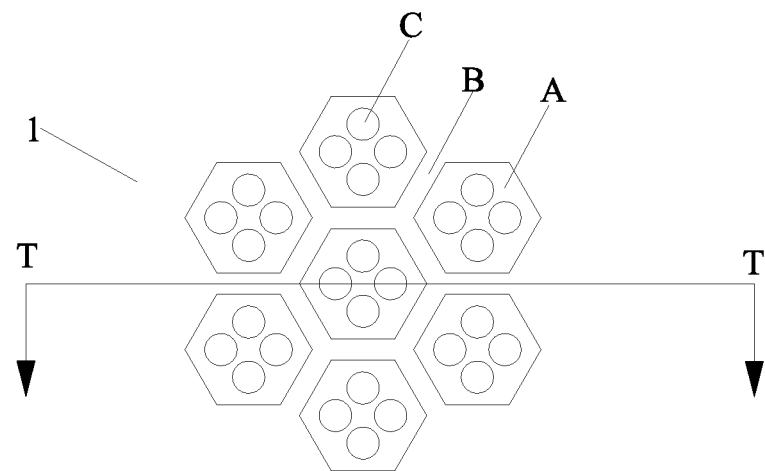
FIG. 5 is a top view of a perforated non-woven fabric in accordance with a fifth embodiment of the present invention.
Figure 5A:
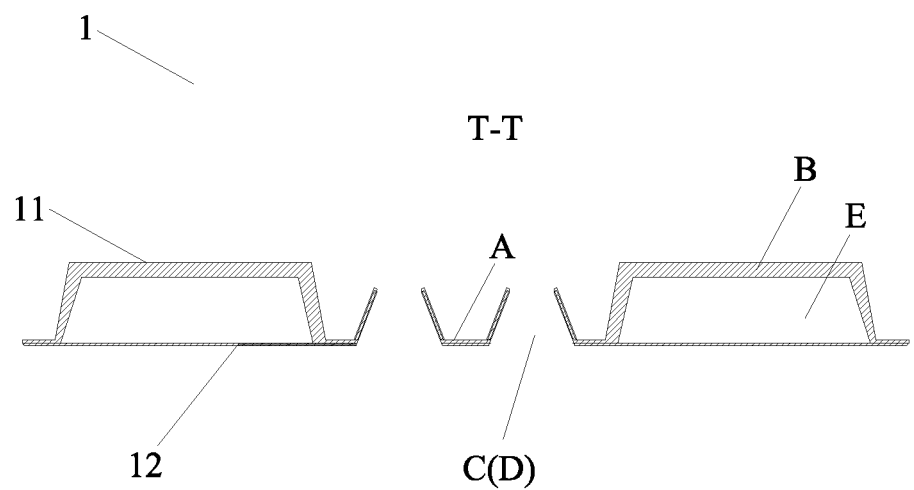
FIG. 5A is a sectional view taken along line T-T of FIG. 5.

As shown in FIG. 5 and FIG. 5A, a perforated non-woven fabric 1 is formed by bonding two perforated non-woven fabric layers 11, 12. The first perforated non-woven fabric layer 11 has a protruding portion B and a recessed portion A to be in contact with the user's skin. Seen from the top view, the protruding portion B is a continuous plane. The recessed portion A is disposed in the protruding portion B in the form of "sea". A three-dimensional funnel-shaped opening C of the first perforated non-woven fabric layer 11 is disposed in the recessed portion A. An upper side of the second perforated non-woven fabric layer 12 is bonded to a lower side of the recessed portion A of the first perforated non-woven layer 12. A three-dimensional funnel-shaped opening D of the second perforated non-woven fabric layer overlaps the three-dimensional funnel-shaped opening C of the first perforated non-woven fabric layer to pass through the entire non-woven fabric 1. The three-dimensional funnel-shaped openings C, D extend from the protruding portion B, the recessed portion A and the bottom surface of the second perforated non-woven fabric layer 12 to the surface. The protruding portion B of the first perforated non-woven fabric layer 11 has a continuous internal space E. The continuous internal space E forms a continuous air flow passage between the first perforated non-woven fabric layer 11 and the second perforated non-woven fabric layer 12 to pass through the entire non-woven fabric 1. The bonding area of the two non-woven fabric layers fixedly supports the air flow passage so that the air flow passage has strong compressive strength. After the pressure is released, the air flow passage is rapidly restored, so that the air flow inside the perforated non-woven fabric 1 convects with the outside air, allowing the air to circulate. In this way, the protruding area in contact with the skin surface can bring a soft touch to the user, maintain the 3D visual effect of the three-dimensional non-woven fabric, reduce the feeling of wetness and stuffiness, and improve the comfort effect. The diameter of the top of the overlapped three-dimensional funnel-shaped openings C, D is 2.0 mm. The diameter R of the top of the three-dimensional funnel-shaped opening is at least 30% greater than the diameter r of the bottom of the three-dimensional funnel-shaped opening. The area of the top of the three-dimensional funnel-shaped opening accounts for 28% of the total area of the perforated non-woven fabric. The three-dimensional funnel-shaped opening has a height of 0.5 mm.

Sixth Embodiment

Figure 6:
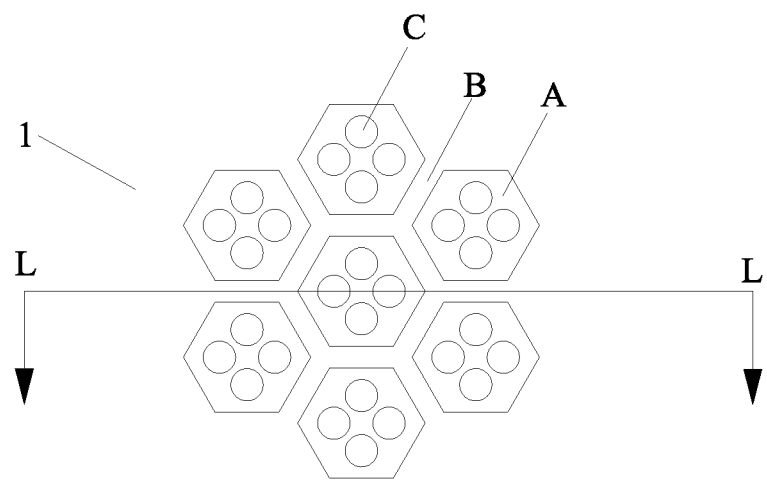
FIG. 6 is a top view of a perforated non-woven fabric in accordance with a sixth embodiment of the present invention.
Figure 6A:
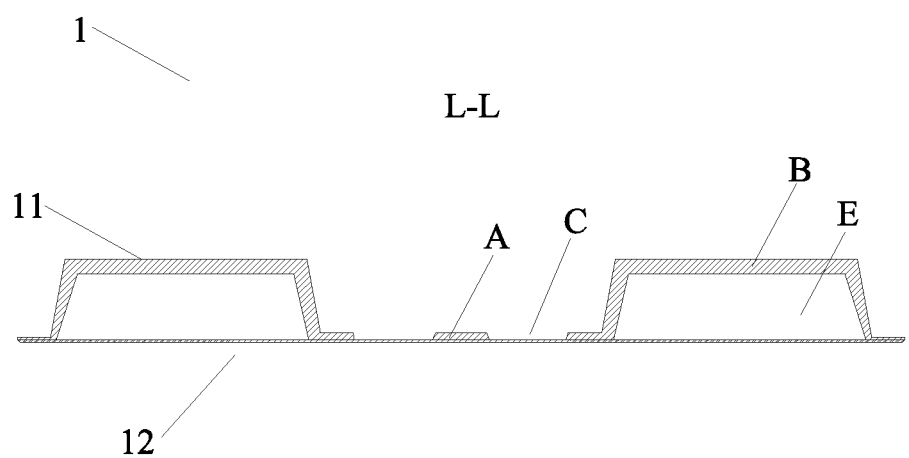
FIG. 6A is a sectional view taken along line L-L of FIG. 6.

As shown in FIG. 6 and FIG. 6A, a perforated non-woven fabric 1 is formed by bonding two perforated non-woven fabric layers 11, 12. The first perforated non-woven fabric layer 11 is a water-repellent non-woven fabric, and the second perforated non-woven fabric layer 12 is a hydrophilic non-woven fabric. The first perforated non-woven fabric layer 11 has a protruding portion B and a recessed portion A to be in contact with the user's skin. Seen from the top view, the protruding portion B is a continuous plane. The recessed portion A is disposed in the protruding portion B in the form of "sea". A three-dimensional funnel-shaped opening C of the first perforated non-woven fabric layer 11 is disposed in the recessed portion A. An upper side of the second perforated non-woven fabric layer 12 is bonded to a lower side of the recessed portion A of the first perforated non-woven layer 12. A three-dimensional funnel-shaped opening D of the second perforated non-woven fabric layer overlaps the three-dimensional funnel-shaped opening C of the first perforated non-woven fabric layer to pass through the entire non-woven fabric 1. The protruding portion B of the first perforated non-woven fabric layer 11 has a continuous internal space E. The continuous internal space E forms a continuous air flow passage between the first perforated non-woven fabric layer 11 and the second perforated non-woven fabric layer 12 to pass through the entire non-woven fabric 1. The bonding area of the two non-woven fabric layers fixedly supports the air flow passage so that the air flow passage has strong compressive strength. After the pressure is released, the air flow passage is rapidly restored, so that the air flow inside the perforated non-woven fabric 1 convects with the outside air, allowing the air to circulate. In this way, the protruding area in contact with the skin surface can bring a soft touch to the user. The diameter of the top of the overlapped three-dimensional funnel-shaped openings C, D is 2.5 mm. The diameter R of the top of the three-dimensional funnel-shaped opening is at least 40% greater than the diameter r of the bottom of the three-dimensional funnel-shaped opening. The area of the top of the three-dimensional funnel-shaped opening accounts for 28% of the total area of the perforated non-woven fabric. The three-dimensional funnel-shaped opening has a height of 1.2 mm. When the feces come into contact with the protruding portion B of the first water-repellent non-woven fabric layer, the soft stool cannot stay on the surface of the operated non-woven fabric layer because of the water-repellent effect, and quickly fall from the protruding portion B to the recessed portion A, and are rapidly infiltrated into the underlying absorbent through the overlapped three-dimensional funnel-shaped openings C, D in the recessed portions to provide a dry effect.

Seventh Embodiment

Figure 7:
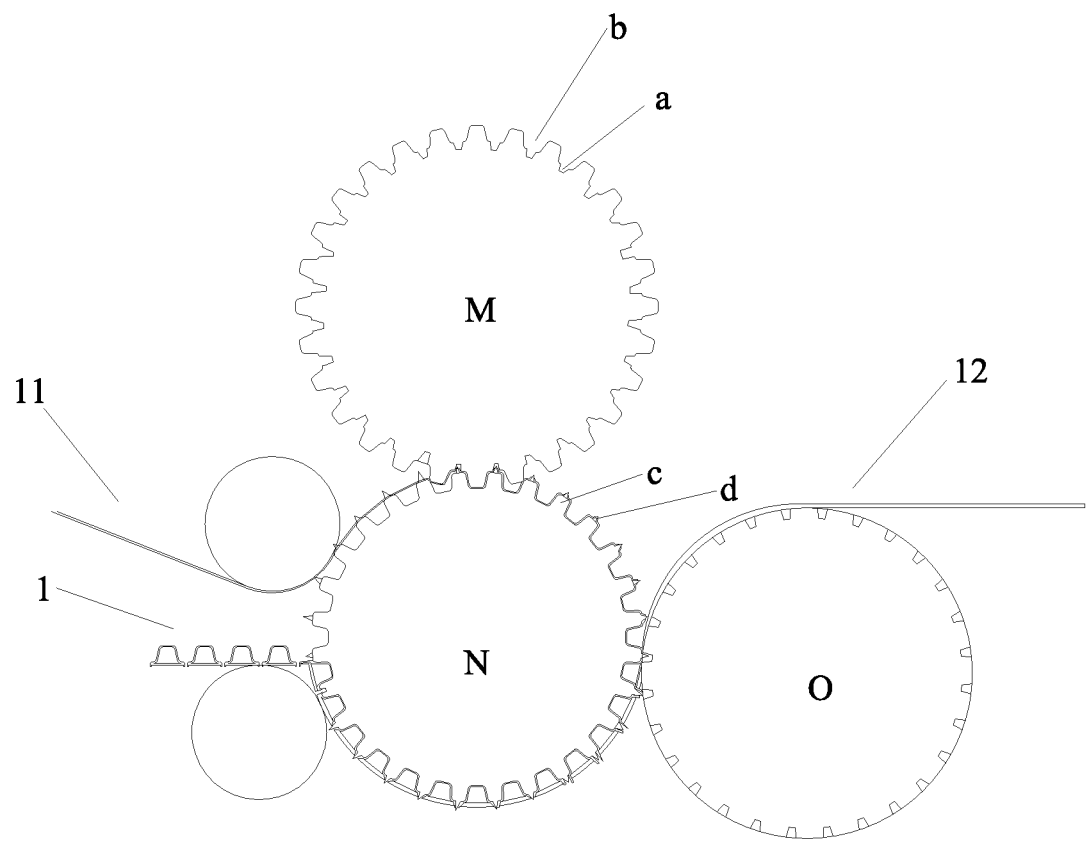
FIG. 7 is a schematic view showing a production method of a perforated non-woven fabric in accordance with a seventh embodiment of the present invention.

FIG. 7, in conjunction with FIG. 1 and FIG. 1A, illustrates an implementation of a perforated non-woven fabric. The first perforated non-woven fabric layer 11 passes through a pair of concave and convex rollers M, N meshing with each other at a speed of 5-100 meter/minute. The temperature of the concave roller M is set in the range of 40-200° C. The temperature of the convex roller N is set in the range of 30-200° C. The concave roller M has a recess b and a recessed hole a in the recess b. The depth of the recess b is in the range of 0.5-45 mm. The depth of the recessed hole a is in the range of 0.5-50 mm. The convex roller N has a protrusion c and a needle tip d on the protrusion c. The height of the protrusion c is in the range of 0.5-50 mm. The height of the needle tip d is in the range of 0.5-45 mm. The gap for the concave roller M and the convex roller N to mesh with each other can be adjusted. The gap is in the range of 0.1-45 mm. During the engagement of the concave roller and the convex roller, the non-woven fabric is pressed and heated by the recess b of the concave roller M and the protrusion c of the convex roller N to form the recessed portion A, and the non-woven fabric is pierced and heated by the recessed hole a of the concave roller M and the needle tip d of the convex roller N to form the three-dimensional funnel-shaped opening C. The concave roller M and the convex roller N mesh with each other and are driven by a transmission mechanism. The concave roller M and the convex roller N are heating rollers. The heating temperature and the gap between the concave roller M and the convex roller N to mesh with each other can be set. The first non-woven fabric layer 11 is heated and compressed by the concave roller M and the convex roller N to form a three-dimensional non-woven fabric having protrusions and openings. After piercing through the needle tip d, the first perforated non-woven fabric layer 11 can be thinly attached to the convex roller N, providing a fast effective positioning effect to decrease energy-consumption greatly. The second perforated non-woven fabric layer 12 passes through the convex roller N to get contact with the first perforated non-woven fabric layer 11, and then both the second perforated non-woven fabric layer 12 and the first perforated non-woven fabric layer 11 pass through the convex roller N and a third concave roller O together. The third concave roller O has a recessed hole fin cooperation with the needle tip d of the convex roller N to pierce and compress the first perforated non-woven fabric layer 11 while the first perforated non-woven fabric layer 11 is wrapped to form the three-dimensional funnel-shaped opening D, and the first perforated non-woven fabric layer 11 is bonded to the second perforated non-woven fabric layer 12. The two non-woven fabric layers are bonded and pierced together to form the two-layer perforated non-woven fabric 1.

Eighth Embodiment

Figure 8:
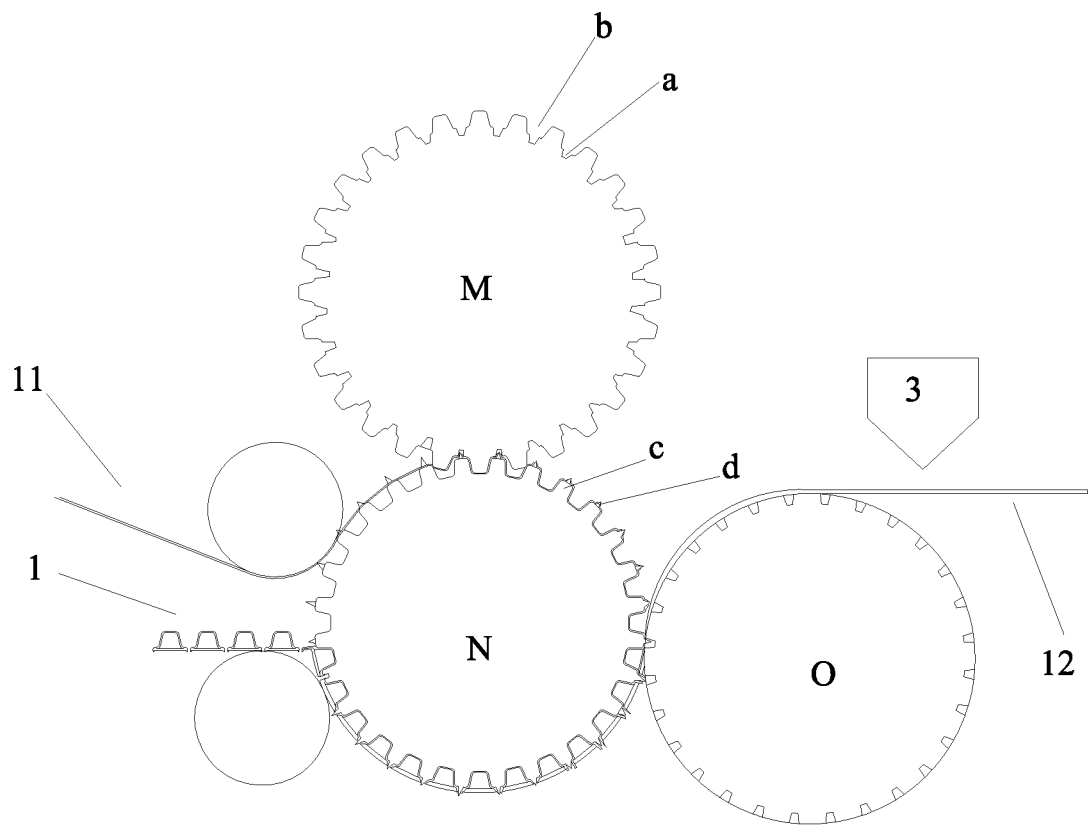
FIG. 8 is a schematic view showing a production method of a perforated non-woven fabric in accordance with an eighth embodiment of the present invention.

FIG. 8, in conjunction with FIG. 1 and FIG. 1A, illustrates another implementation of a perforated non-woven fabric. The first perforated non-woven fabric layer 11 passes through a pair of concave and convex rollers M, N meshing with each other at a speed of 5-100 meter/minute. The temperature of the concave roller M is set in the range of 40-200° C. The temperature of the convex roller N is set in the range of 30-200° C. The concave roller M has a recess b and a recessed hole a in the recess b. The depth of the recess b is in the range of 0.5-45 mm. The depth of the recessed hole a is in the range of 0.5-50 mm. The convex roller N has a protrusion c and a needle tip d on the protrusion c. The height of the protrusion c is in the range of 0.5-50 mm. The height of the needle tip d is in the range of 0.5-45 mm. The gap for the concave roller M and the convex roller N to mesh with each other can be adjusted. The gap is in the range of 0.1-45 mm During the engagement of the concave roller and the convex roller, the non-woven fabric is pressed and heated by the recess b of the concave roller M and the protrusion c of the convex roller N to form the recessed portion A, and the non-woven fabric is pierced and heated by the recessed hole a of the concave roller M and the needle tip d of the convex roller N to form the three-dimensional funnel-shaped opening C. The concave roller M and the convex roller N mesh with each other and are driven by a transmission mechanism. The concave roller M and the convex roller N are heating rollers. The heating temperature and the gap between the concave roller M and the convex roller N to mesh with each other can be set. The first non-woven fabric layer 11 is heated and compressed by the concave roller M and the convex roller N to form a three-dimensional non-woven fabric having protrusions and openings and is attached to the convex roller N. After piercing through the needle tip d, the first perforated non-woven fabric layer 11 can be firmly attached to the convex roller N, providing a fast effective positioning effect to decrease energy-consumption greatly. The second perforated non-woven fabric layer 12 is glued on the surface through a gluing device 3 to pass through the convex roller N to get contact with the first perforated non-woven fabric layer 11, and then both the second perforated non-woven fabric layer 12 and the first perforated non-woven fabric layer 11 pass through the convex roller N and a third concave roller O together. The third concave roller O has a recessed hole fin cooperation with the needle tip d of the convex roller N to pierce and compress the first perforated non-woven fabric layer 11 while the first perforated non-woven fabric layer 11 is wrapped to form the three-dimensional funnel-shaped opening D. The two non-woven fabric layers are bonded together by gluing to form the two-layer perforated non-woven fabric 1.

Ninth Embodiment

Figure 9:
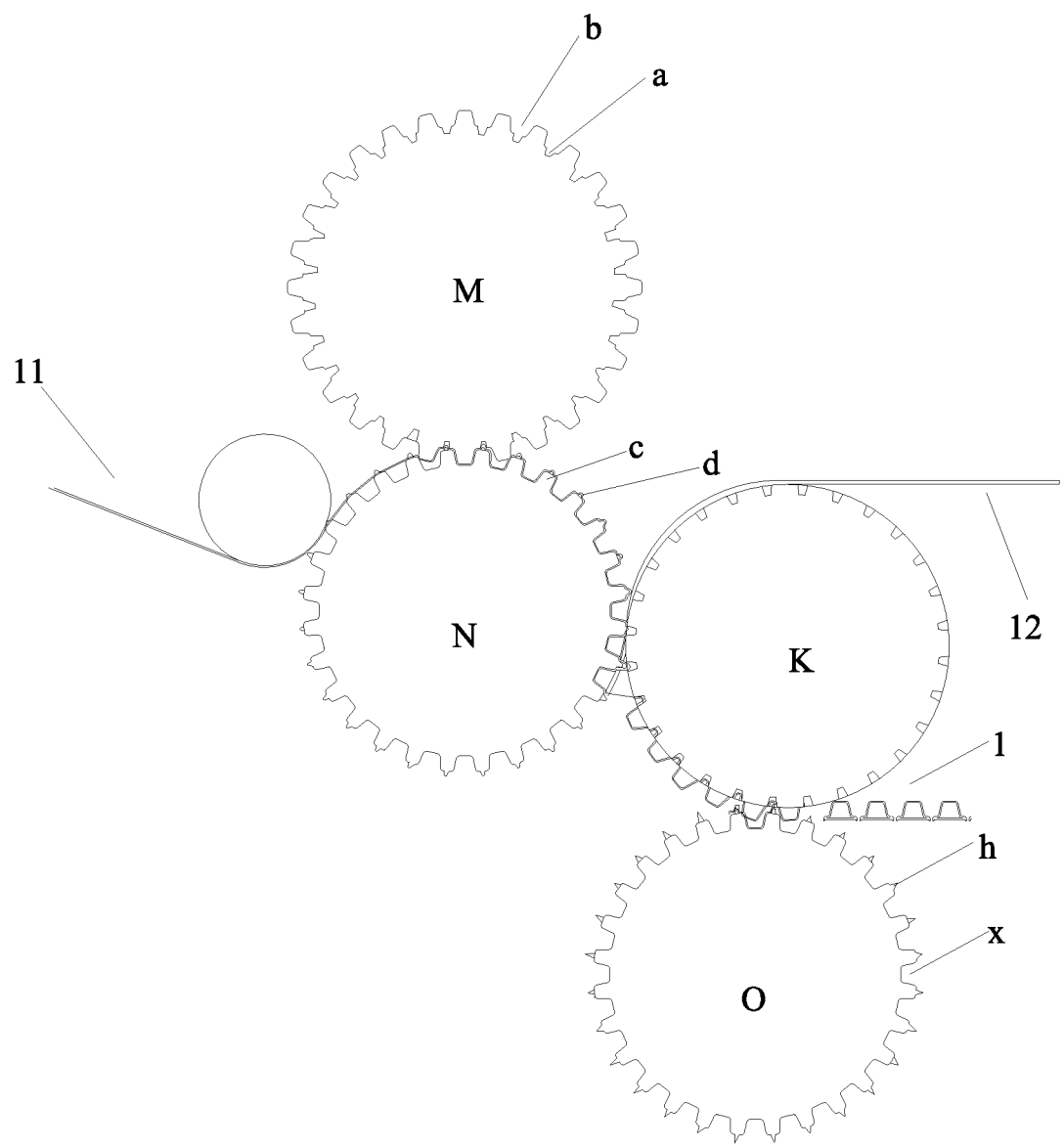
FIG. 9 is a schematic view showing a production method of a perforated non-woven fabric in accordance with a ninth embodiment of the present invention.

FIG. 9, in conjunction with FIG. 1 and FIG. 1A, illustrates a further implementation of a perforated non-woven fabric. The first perforated non-woven fabric layer 11 passes through a pair of concave and convex rollers M, N meshing with each other at a speed of 5-100 meter/minute. The temperature of the concave roller M is set in the range of 40-200° C. The temperature of the convex roller N is set in the range of 306-200° C. The concave roller M has a recess b and a recessed hole a in the recess b. The depth of the recess b is in the range of 0.5-45 mm. The depth of the recessed hole a is in the range of 0.5-50 mm. The convex roller N has a protrusion c and a salient point d on the protrusion c. The height of the protrusion c is in the range of 0.5-50 mm. The height of the salient point d is in the range of 0.5-45 mm. The gap for the concave roller M and the convex roller N to mesh with each other can be adjusted. The gap is in the range of 0.1-45 mm During the engagement of the concave roller and the convex roller, the non-woven fabric is pressed and heated by the recess b of the concave roller M and the protrusion c of the convex roller N to form the recessed portion A, and the non-woven fabric is pressed and heated by the recessed hole a of the concave roller M and the salient point d of the convex roller N to form a preset three-dimensional funnel-shaped opening C1. The concave roller M and the convex roller N mesh with each other and are driven by a transmission mechanism. The concave roller M and the convex roller N are heating rollers. The heating temperature and the gap between the concave roller M and the convex roller N to mesh with each other can be set. The first non-woven fabric layer 11 is heated and compressed by the concave roller M and the convex roller N to form a three-dimensional non-woven fabric having protrusions and preset openings and is attached to the convex roller N.

The second perforated non-woven fabric layer 12 passes through the convex roller N to get contact with the first perforated non-woven fabric layer 11, and then both the second perforated non-woven fabric layer 12 and the first perforated non-woven fabric layer 11 pass through the convex roller N and a roller K together. The roller K has a recessed hole f to mate with the salient point d of the convex roller N. The first perforated non-woven fabric layer 11 and the second perforated non-woven fabric layer 12 pass through the convex roller N and the roller K together to be heated, compressed and bonded together to form a three-dimensional non-woven fabric having preset openings, and then transfer to the roller K, and finally pass through the K roller and a third concave roller O. The third concave roller O has a recess x and a needle h to mate with the roller K. The protruding portion A enters the recess x. The needle h pierces the two non-woven fabric layers simultaneously to form the perforated non-woven fabric 1 with the three-dimensional funnel-shaped openings C, D.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A perforated non-woven fabric, the perforated non-woven fabric being formed by overlapping three-dimensional funnel-shaped openings of first and second perforated non-woven fabric layers such that the three-dimensional funnel shapes of the three-dimensional funnel-shaped openings of the first and second perforated non-woven fabric layers overlap each other, wherein each of the three-dimensional funnel shapes of the first perforated non-woven fabric layer defines a first funnel and each of the three-dimensional funnel shapes of the second perforated non-woven fabric layer defines a second funnel, the first funnel being totally contained in the second funnel so as to have the first and second funnels overlap each other; the first perforated non-woven fabric layer having a protruding portion and a recessed portion, the protruding portion having an internal space; an upper side of the second perforated non-woven fabric layer being bonded to a lower side of the recessed portion of the first perforated non-woven layer; the overlapped three-dimensional funnel-shaped openings passing through the first perforated non-woven fabric layer and the second perforated non-woven fabric layer.

2. The perforated non-woven fabric as claimed in claim 1, wherein an upper surface of the protruding portion forms a continuous plane so that a continuous air flow passage is formed between the continuous internal space of the protruding portion of the first perforated non-woven fabric layer and the second perforated non-woven fabric layer.

3. The perforated non-woven fabric as claimed in claim 1, wherein the protruding portion and the recessed portion are arranged by turns, the protruding portion has an independent discontinuous internal space, and an independent discontinuous air flow passage is formed between the independent discontinuous internal space of the protruding portion of the first perforated non-woven fabric layer and the second perforated non-woven fabric layer.

4. The perforated non-woven fabric as claimed in claim 1, wherein the protruding portion of the first perforated non-woven fabric layer has an opening structure.

5. The perforated non-woven fabric as claimed in claim 1, wherein the three-dimensional funnel-shaped openings each extend from a top thereof toward a bottom thereof.

6. The perforated non-woven fabric as claimed in claim 1, wherein the three-dimensional funnel-shaped openings each extend from a bottom thereof toward a top thereof.

7. The perforated non-woven fabric as claimed in claim 1, wherein a diameter of a top of the three-dimensional funnel-shaped openings is 0.2-5 mm.

8. The perforated non-woven fabric as claimed in claim 1, wherein a diameter of a top of the three-dimensional funnel-shaped openings is at least 20% greater than a diameter of a bottom of the three-dimensional funnel-shaped openings.

9. The perforated non-woven fabric as claimed in claim 1, wherein the area of a top of the three-dimensional funnel-shaped openings accounts for less than 70% of the total area of the perforated non-woven fabric.

10. The perforated non-woven fabric as claimed in claim 1, wherein the three-dimensional funnel-shaped openings have a height of 0.1-5 mm.

11. The perforated non-woven fabric as claimed in claim 1, wherein the first perforated non-woven fabric layer is a water-repellent non-woven fabric, and the second perforated non-woven fabric layer is a hydrophilic non-woven fabric.

12. The perforated non-woven fabric as claimed in claim 1, wherein the first perforated non-woven fabric layer or/and the second perforated non-woven fabric layer are one of a hot-blast non-woven fabric, a spunbond non-woven fabric and a spunlace non-woven fabric.

13. The perforated non-woven fabric as claimed in claim 1, wherein the bonding of the recessed portion is a thermal bonding region or a glue bonding region.

* * * * *